United States Patent
Barbieri et al.

(10) Patent No.: US 6,896,703 B2
(45) Date of Patent: May 24, 2005

(54) EXPANDABLE SOCKET

(75) Inventors: Enzo Barbieri, Fucecchio (IT); Renzo Renzini, Castiglion Fiorentino (IT); Anton Cotting, Grenchen (CH); Peter Christen, Selzach (CH); Daniel Delfosse, Bern (CH)

(73) Assignee: Mathys Medizinaltechnik AG, Bettlach (CH)

( * ) Notice: Subject to any disclaimer, the term of this patent is extended or adjusted under 35 U.S.C. 154(b) by 4 days.

(21) Appl. No.: 10/470,454

(22) PCT Filed: Oct. 19, 2001

(86) PCT No.: PCT/EP01/12130
§ 371 (c)(1),
(2), (4) Date: Jul. 25, 2003

(87) PCT Pub. No.: WO02/058598
PCT Pub. Date: Aug. 1, 2002

(65) Prior Publication Data
US 2004/0093090 A1 May 13, 2004

(30) Foreign Application Priority Data
Jan. 26, 2001 (DE) .......................................... 101 03 482

(51) Int. Cl.[7] .................................................. A61F 2/32
(52) U.S. Cl. ................. 623/22.3; 623/22.32; 623/22.38; 623/22.23
(58) Field of Search .......................... 623/22.32, 22.38, 623/22.3, 22.23, 22.35, 22.36, 22.37, 22.26

(56) References Cited

U.S. PATENT DOCUMENTS

| | | | | | |
|---|---|---|---|---|---|
| 3,840,904 | A | * | 10/1974 | Tronzo | 623/22.32 |
| 4,834,759 | A | * | 5/1989 | Spotorno et al. | 623/22.3 |
| 5,108,448 | A | * | 4/1992 | Gautier | 623/22.26 |

FOREIGN PATENT DOCUMENTS

| | | | | | |
|---|---|---|---|---|---|
| EP | 0169978 | * | 2/1986 | | A61F/2/34 |
| EP | 0456580 | * | 11/1991 | | A61F/2/32 |
| FR | 2628314 | * | 9/1989 | | A61F/2/32 |

* cited by examiner

*Primary Examiner*—Paul B. Prebilic
(74) *Attorney, Agent, or Firm*—Scully, Scott, Murphy & Presser

(57) ABSTRACT

The invention relates to an expandable socket (1) for a hip joint endoprosthesis able to be cementlessly anchored in place which is at least approximately hemispherical and which is provided with a plurality of slots (3) extending in a meridional direction, thus forming intervening tongues (4), on which are formed projections (5) that form a plurality of rows (6; 6a, 6b) extending from an equator (2) of the expandable socket (1). The projections (5) are arranged on the tongues (4) in such a manner that a row (6a) of projections (5) arranged in the center of the tongue (4) extends on a meridian (14) of the hemispherical socket (1) while at least one adjoining row (6b) of projections (5) extends in a line that extends at all points in parallel to the meridian (14) of the row (6a) of projections (5) arranged in the center and not through a pole (10) of the hemispherical expandable socket (1).

12 Claims, 1 Drawing Sheet

EXPANDABLE SOCKET

The invention relates to an expandable socket to form a connecting joint between two human or animal bones.

Known from EP 0 169 978 B1 is an endoprosthesis for a hip joint socket which is suitable for cementless anchoring and which comprises an inner socket body and an outer cup, in which the socket body is provided with a conical sheath and the outer cup with a cavity matched to the sheath, the outer cup and socket body being held in one another via a locking structure, there also being a number of slots extending in a meridional direction uniformly distributed over the circumference of the outer cup, which latter is at least approximately hemispherical in shape externally, the surface of the outer cup further being provided with a structure made up of projections.

Also known, from EP 0 242 633 B1, is an endoprosthesis for a hip joint socket which is suitable for cementless anchoring and which comprises an inner cup body and an outer shell, and which is similar in construction to the endoprosthesis known from EP 0 169 978 B1 and has, in the region of the surface of the outer shell close to the equator, a structure composed of projections arranged in a plurality of peripheral rows.

The projections in EP 0 242 633 B1 are spike-like in shape and are arranged in concentric circles on the surface of the expandable socket. The projections in EP 0 169 978 B1 are pin-like in shape and are mounted on the surface of the expandable socket or are inserted thereinto in suitable openings.

What is disadvantageous about the expandable sockets for hip joint endoprostheses known from the above-mentioned printed publications is in particular that the projections are so arranged on the expandable socket that forces which act in the direction opposite to that in which the expandable socket was implanted in the bone tissue may cause the expandable socket to detach from the bone tissue. This is encouraged in particular by the fact that the projections are arranged on the surface of the hemisphere along meridians which, in a similar way to the meridians on a globe, all meet at a point, namely the pole of the hemisphere.

What is more, the shape selected for the projections is unhelpful, because, as they penetrate into the spongiose bone tissue, they may result on the one hand in areas of compression and on the other in holes. This has an adverse effect on the retaining force in the bone tissue, as a result of which it may likewise happen that the expandable socket comes loose from the spongiose tissue.

It is therefore an object of the invention to provide a surface structure whose projections, on penetration into the bone, on the one hand provide compression of the tissue displaced by them which is uniform on all sides and on the other provide at all points the prerequisites for good adhesion and growing-on of the tissue. The structure formed by the projections should further be such that the retaining force in spongiose tissue is increased by the special layout of the projections.

The object is achieved in accordance with the invention by arranging the projections on tongues of the expandable socket in such a manner that rows of projections arranged in the centre of the tongue extend on a meridian of the hemispherical socket while at least one adjoining row of projections extends in a line that extends in parallel to the meridian of the rows arranged in the centre and not through the pole of the hemispherical expandable socket.

In the preferred embodiment the number of rows of projections on the tongues, which tongues are separated from one another by meriodionally extending slots, is three.

The projections in the three rows on each of the tongues are preferably equally spaced.

With increasing distance from an equator of the expandable socket, the projections advantageously rise decreasingly high above the surface of the expandable socket. The height of the projections is optimised in the light of the geometry of the compressed expandable socket when being inserted in the bone in such a way that the projections are prevented from hitting against and cutting into the bone.

The projections in the centre row are symmetrically shaped, whereas those in the adjoining rows are asymmetrically shaped. In particular, the flanks of the projections in the centre row are perpendicular to the surface of the expandable socket, whereas those of the projections in the adjoining rows make an angle with the surface of the expandable socket which is more than 90°.

For easier implantation, the expandable socket has at its equator a radially inwardly inclined bevel on the tongues. In the region of the equatorial bevel, a groove is advantageously provided in each tongue. The groove acts as a stabilising means for the anti-friction member inserted in the expandable socket. In the preferred embodiment, the disposition of the grooves allows an anti-friction member which is not symmetrical in rotation to be adjusted interoperatively to the characteristics of the site of the operation, in which case the anti-friction member can be rotated through an angle of 30° at a time and inserted.

The invention is described in detail below by reference to a preferred embodiment and to the drawings. In the drawings.

Figure 1:
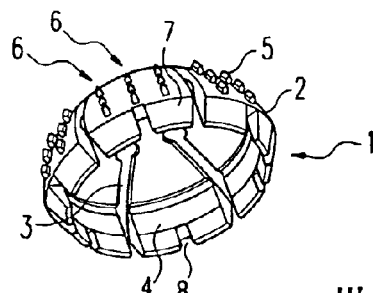
FIG. 1 is a diagrammatic general arrangement view of an embodiment of expandable socket according to the invention.

FIG. 1 is a perspective general arrangement view of an embodiment of expandable socket 1 according to the invention. The expandable socket 1 is to be used in this case in particular as part of an endoprosthesis, a hip prosthesis for example, in which case an anti-friction member, which may be composed of plastics material for example and which is fitted onto the condyle of the hip joint, is inserted in the expandable socket 1.

In FIG. 1 the expandable socket 1 is shown in a perspective view looking from the side and below. It has a plurality of slots 3 which run in the meridional direction from an equator 2 of the expandable socket 1, which is at least approximately hemispherical in shape, which slots 3 extend from the equator 2 of the expandable socket 1 in the direction of its pole, which is not visible in FIG. 1. The slots 3 divide at least the part of the expandable socket 1 which is close to the equator into tongues 4 which, in the present embodiment, are equal in number to the meridional slots 3. At least in the equatorial region, the slots 3 give the expandable socket 1 a certain elasticity, which makes it possible for the expandable socket 1 to be implanted in suitably prepared bone tissue of the pelvis with the help of a suitable implantation instrument (not shown).

Arranged on the outside of the tongues 4 in rows 6 are projections 5. In the present embodiment three rows 6 of projections 5 are arranged on each tongue 4. The projections 5 are so arranged and shaped in this case that they make it possible for the expandable socket 1 to be cementlessly anchored in place, chiefly in the spongiose tissue of the pelvis.

At the equator 2 of the expandable socket 1, the tongues 4 have a bevel 7 which is inclined radially inwards. The tongues 4 also each have, in the region of the bevel 7, at least one groove 8.

Figure 2:
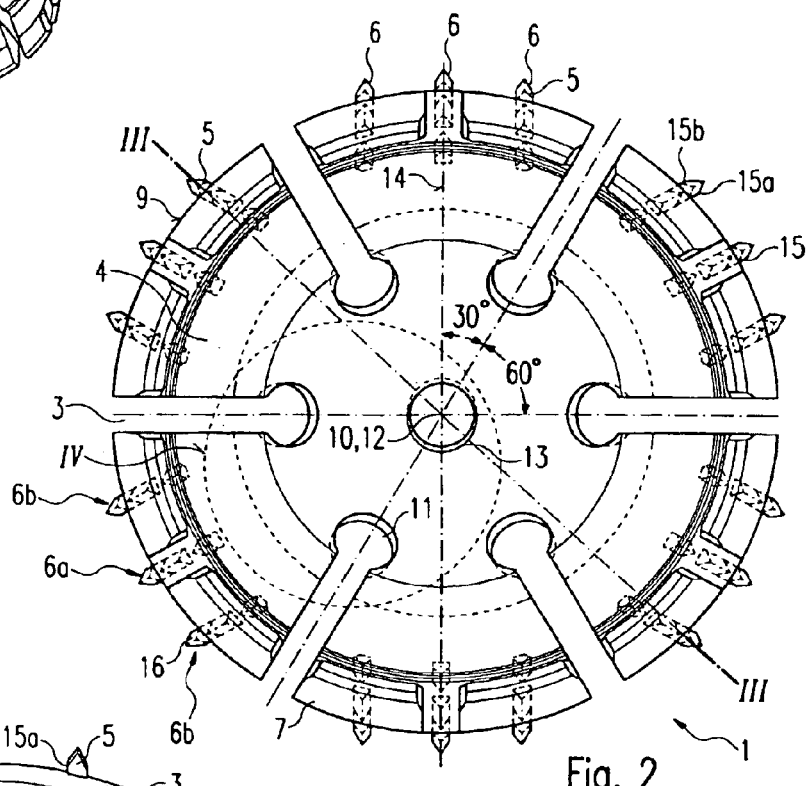
FIG. 2 is a diagrammatic plan view, looking from the equator towards the pole, of the expandable socket according to the invention seen in FIG. 1.

FIG. 2 is a diagrammatic plan view of the expandable socket 1 arranged in accordance with the invention, looking from the equator 2 towards the pole 10. In the present preferred embodiment, the expandable socket 1 according to the invention has six meridional slots 3 and the same number of intervening tongues 4 which are separated from one another by the slots 3. Each of the tongues 4 comprises, as already indicated in FIG. 1, three rows 6 of projections 5 which are arranged on an outer surface 9 of the expandable socket 1.

At their ends close to the pole, the meridional slots 3 have circular widenings 11 which allow for the forces exerted by the instrument at the time of implantation.

Provided at the pole 10 of the expandable socket 1 is a bore 12, which may for example have a thread 13. This latter may for example be used to fix the expandable socket 1 to the implantation instrument.

The special shape and disposition of the projections 5 on the surface 9 of the expandable socket 1 merit particular attention. For a better understanding of the disposition according to the invention of the projections 5 on the expandable socket 1 it is useful for FIGS. 1 and 2 to be considered together. On the tongue 4 of the expandable socket 1 which is facing the viewer in FIG. 1 can be seen three rows 6 of projections 5. A centre row 6a is flanked by two adjoining rows 6b in this case. The centre row 6a is arranged on a meridian 14 of the hemispherical expandable socket 1 in this case. The meridian 14 runs through the pole 10 of the expandable socket 1 in this case in a way comparable to the meridians on a globe. The adjoining rows 6b of projections 5 are arranged on lines parallel to the meridian 14 which at all points extend in parallel to the meridian 14 and thus do not intersect the pole 10 of the expandable socket 1. All the rows 6 of projections 5 are perpendicular to the equator 2 of the expandable socket 1.

In the present embodiment there are six meridional slots 3, six tongues 4 and six meridians 14, on which latter the centre rows 6a of projections are arranged. The meridional slots 3 are each placed at an angular spacing of 60°, which means that the meridians 14 carrying the six centre rows too make an angle of 60° with one another. The meridians 14 are each offset from the meridional slots 3 at an angle of 30°.

Because the projections are arranged in three mutually parallel rows 6, the distance between the projections 5 and the meridional slots 3 becomes smaller with increasing distance from the equator 2 of the expandable socket 1. This can clearly be seen in FIG. 2 from the projections 5 indicated in dashed lines which, in the view shown in FIG. 2, are hidden behind the curve of the hemispherical expandable socket 1. In the present embodiment there are in each case two further projections 5 arranged above the equatorial projections 5. There are thus nine projections 5 provided per tongue 4. From the equator 2 of the expandable socket 1 towards the pole 10 of the expandable socket 1, the projections 5 are arranged in concentric circles which become smaller in diameter from the equator 2 to the pole 10.

The shape of the projections 5 in cross-section is a rectangle surmounted by a roof-like triangle, which in three dimensions means a parallelepiped surmounted by a three-edge prism. The projections 5 in the centre row 6a are symmetrical in shape in this case, i.e. the flanks 15 of the projections 5 in the centre row 6a are equal in length and form an angle of 90° with the surface 9 of the expandable socket 1. The projections 5 in the adjoining rows 6b are arranged to have their axes parallel to those of the projections 5 in the centre row 6a. What this means is that those flanks 15a of the projections 5 in the adjoining rows 6b which face towards the centre row 6a are shorter than the flanks 15b which face away from the centre row 6a and that the flanks 15b form an angle of more than 90° with the surface 9 of the expandable socket 1. The flanks 15a accordingly make an angle of less than 90° with the surface 9 of the expandable socket 1. Hence both the rows 6 in which the projections are arranged and the axes of the projections 5 on each tongue 4 are aligned parallel to one another.

In the plan view looking from the equator 2 to the pole 10 of the expandable socket 1 which is shown in FIG. 2 can be seen end-wall faces 16 of the projections 5. The inclination of the end-wall faces 16 of the projections 5 is so selected in this case that the projections 5 are slightly inclined to a direction of implantation of the expandable socket 1. In the expanded state, a slightly undercut space is thus formed in the direction of implantation. If the expandable socket 1 is clamped into the implantation instrument (not shown), then the projections are no longer inclined away from the direction of implantation. What can be achieved in this way is that the tissue is not heavily compressed in the region of the projections 5 at the time of implantation nor are cavities left in the tissue after the implantation, or rather after the expansion of the expandable socket 1 into it, which might mean that the bone would grow in less satisfactorily. For each tongue 4, the axis of rotation when the expandable socket 1 which has been compressed for insertion opens out is situated on the line connecting the pairs of adjoining circular widenings 11.

The advantage of the projections 5 arranged in parallel rows 6a and 6b becomes clear when the results of a tensile force in the opposite direction to the direction of implantation of the expandable socket 1 are considered. This tensile force may for example be exerted on the implant by intrinsic weight of the leg affected.

If, as is known from the prior art, the rows 6a and 6b of projections 5 were all arranged on meridians 14, there would be a greater danger of the expandable socket 1 slipping out of the spongiose bone tissue as a result of the projections 5 being arranged one behind the other. The projections 5 arranged in parallel rows 6 are, however, arranged not one behind the other but with a lateral offset. In this way, when there are projections 5 arranged on meridians, the resistance to any tensile movement is spread, in the region of the adjoining rows 6b, from a projection 5 on the equator of the expandable socket 1 to all three projections 5 in each of the adjoining rows 6b on the right and left, which means that the resulting number of projections 5 which, on each tongue 4, hold the expandable socket 1 in the tissue in opposition to a tensile force is increased from three to seven. The fact that the individual projections 5 in the adjoining rows 6b are arranged on an axis parallel to that of the centre row 6a has an additional supporting effect. The ability which the expandable socket 1 has to be held in place in the spongiose tissue of the hip is considerably increased in this way.

Figure 3:
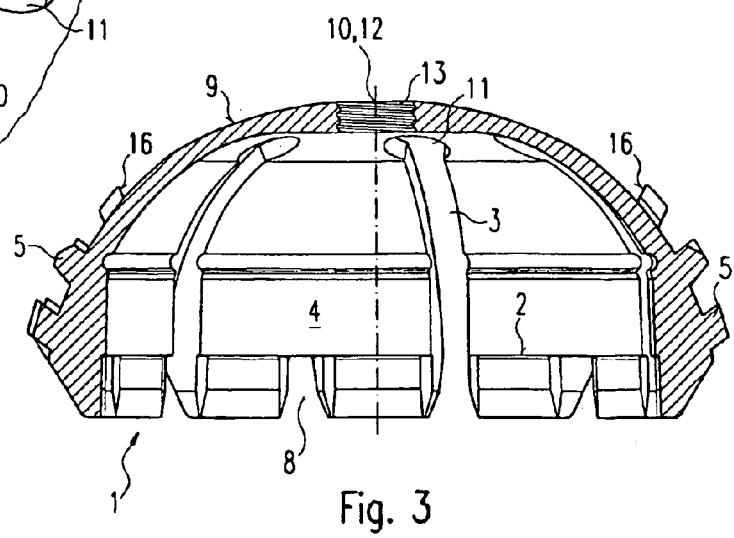
FIG. 3 is a diagrammatic longitudinal section through the expandable socket according to the invention along line III—III in FIG. 2.

FIG. 3 is a sectional view through the expandable socket 1 according to the invention on a line III—III in FIG. 2. The sectioned hemisphere of the expandable socket 1 has been included as a background to the drawing in this case to make things clearer.

The slightly undercut form taken by the projections 5 which was mentioned above can clearly be seen in FIG. 3. The undercut is selected to be such in that case that the projections 5 are slightly undercut in the direction of implantation when the expandable socket 1 is in the relaxed state, which they no longer are when the expandable socket 1 is in the tensioned state when, say, it is clamped into the implantation instrument[1]. In the course of the implantation the projections 5 lie in the direction of implantation, i.e. penetrate straight into the bone tissue of the hip. If the implantation instrument is then removed, the expandable socket 1 expands into the spongiose tissue and in do doing drives the projections 5 in at an angle of slightly more than 90°. The compression of the tissue or the formation of cavities due to too great an undercut, which may result in the spongiose tissue not growing round fully, is avoided by this means.

[1]Translator's note: I found it difficult to understand exactly what is being said here. The conclusion I reached was that what is meant is that the faces of the projections which lead in the direction of implantation are undercut when the socket is relaxed (FIG. 3) but when it is tensed and the tongues are curved inwards these faces swing down and line up at right angles to the main axis.

It can also be seen from FIG. 3 that, except in the centre row 6a, the projections 5 are arranged not on meridians but on parallel lines which do not intersect the pole 10 of the expandable socket 1. This is particularly clearly seen in the right-hand part of FIG. 3, where the projection 5 lying closest to the pole 10 is shown not to be intersected, the next one is shown to be partly intersected and the projection 5 lying closest to the equator 2 is shown to be completely intersected.

If the projections 5 in the rows 6b were arranged on meridians, they would all be intersected.

Figure 4:
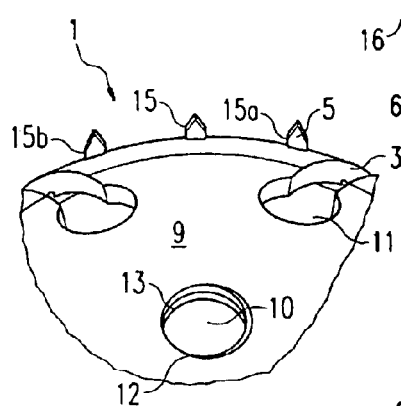
FIG. 4 is a partial perspective view of the expandable socket arranged in accordance with the invention in the area marked IV in FIG. 2.

FIG. 4 is a partial perspective view of the expandable socket 1 arranged in accordance with the invention in the region IV indicated in FIG. 2, the asymmetrical shape of the projections 5, which are aligned in the adjoining rows 6b on axes parallel to that of the projections 5 in the centre row 6a, being shown with particular clarity in this case.

The flanks 15 of the projections 5 in the centre row 6a are perpendicular to the surface of the expandable socket 1 in this case, whereas the flanks 15a and 15b of the projections 5 in the adjoining rows make angles with the surface of the expandable socket which are respectively less than and more than 90°.

The invention is not limited to the embodiment shown and is for example also suitable for expandable sockets 1 having different numbers of meridional slots 3 and tongues 4 and also for shapes of expandable socket 1 which are other than spherical.

What is claimed is:

1. Expandable socket for a joint endoprosthesis able to be cementlessly anchored in place, the expandable socket being at least approximately hemispherical in shape and being provided with a plurality of slots extending in a meridional direction, thereby forming intervening tongues on which are formed projections which form a plurality of rows extending from an equator of the expandable socket wherein the projections are arranged on the tongues in such a manner that a row of projections arranged in the center of the tongue extends on a meridian of the hemispherical expandable socket while at least one adjoining row of projections extends in a line that extends in parallel at all points to the meridian of the row of projections arranged in the center and not through a pole of the hemispherical expandable socket.

2. Expandable socket according to claim 1, wherein the number of rows of projections is three for each said tongue.

3. Expandable socket according to claim 2, wherein the spacings of the projections in the three rows on each tongue are the same.

4. Expandable socket according to any one of claims 1 to 3, wherein the projections are arranged on concentric parallels of latitude.

5. Expandable socket according to any one of claims 1 to 3, wherein a height of the projections above an outer surface (9) of the expandable socket becomes smaller as the distance of the projections from the equator of the expandable socket becomes larger.

6. Expandable socket according to any one of claims 1 to 3, wherein the projections are in the form of a parallelepiped surmounted by a three-edged prism.

7. Expandable socket according to claim 6, wherein the projections in the center row are symmetrical in shape.

8. Expandable socket according to claim 6, wherein the projections in the rows adjoining the center row are a symmetrical in shape.

9. Expandable socket according to claim 6, wherein the projections are arranged on the tongues such that the row of projections arranged centrally on the tongues stands perpendicularly on the surface of the expandable socket (1) and flanks of the parallelepiped parts of the projections each subtend an angle of approximately 90° with said surface (9).

10. Expandable socket according to claim 6, wherein the projections in the rows adjoining the center row are parallel to the projections in the center row (6a) and the flanks (15b) of the parallelepiped parts of the projections subtend an angle of more than 90° with the surface of the expandable socket.

11. Expandable socket according to claim 1, wherein at said equator the expandable socket has a radially inwardly inclined bevel on the tongues.

12. Expandable socket according to claim 11, wherein the tongues each have a groove in the region of the equatorial bevel.

\* \* \* \* \*